US006998395B2

(12) United States Patent
Jackson et al.

(10) Patent No.: US 6,998,395 B2
(45) Date of Patent: Feb. 14, 2006

(54) ADMINISTRATION OF ESTRADIOL METABOLITES FOR THE TREATMENT OR PREVENTION OF OBESITY, METABOLIC SYNDROME, DIABETES, AND VASCULAR AND RENAL DISORDERS

(75) Inventors: Edwin K. Jackson, Pittsburgh, PA (US); Stevan P. Tofovic, Pittsburgh, PA (US); Raghvendra K. Dubey, Glenshaw, PA (US)

(73) Assignee: University of Pittsburg,, Pittsburgh, PA (US)

( * ) Notice: Subject to any disclaimer, the term of this patent is extended or adjusted under 35 U.S.C. 154(b) by 6 days.

(21) Appl. No.: 10/222,962

(22) Filed: Aug. 19, 2002

(65) Prior Publication Data
US 2003/0050294 A1 Mar. 13, 2003

Related U.S. Application Data

(60) Provisional application No. 60/312,741, filed on Aug. 17, 2001.

(51) Int. Cl.
A61K 31/56 (2006.01)
(52) U.S. Cl. .................................. 514/182
(58) Field of Classification Search ............. 514/182
See application file for complete search history.

(56) References Cited

U.S. PATENT DOCUMENTS

| 5,736,154 A | 4/1998 | Fuisz |
| 5,788,980 A | 8/1998 | Nabahi |
| 5,827,531 A | 10/1998 | Morrison et al. |
| 5,830,506 A | 11/1998 | Taylor |
| 5,874,098 A | 2/1999 | Stevens et al. |
| 5,977,096 A | 11/1999 | Droescher et al. |
| 6,071,544 A | 6/2000 | Sunvold |
| 6,103,256 A | 8/2000 | Nabahi |
| 6,143,716 A | 11/2000 | Meers et al. |
| 6,238,284 B1 | 5/2001 | Dittgen et al. |
| 6,251,418 B1 | 6/2001 | Ahern et al. |
| 6,339,069 B1 | 1/2002 | Meers et al. |
| 6,367,929 B1 | 4/2002 | Maiden et al. |
| 6,372,248 B1 | 4/2002 | Qin et al. |
| 6,372,813 B1 | 4/2002 | Johnson et al. |
| 6,555,530 B1 * | 4/2003 | Wassermann ............... 514/178 |

FOREIGN PATENT DOCUMENTS

WO   WO 99/48502   *   9/1999

OTHER PUBLICATIONS

Dubey et al., "Estradiol Metabolites Inhit Endothelin Synthesis by an Estrogen Receptor-Independent Mechanism." Hypertension, vol. 37, pp. 640-644, 2001.*
Mokdad, A.H., et al., J. Am. Medical Assoc. 284:1650 (2000).
Grundy, S.M., Endocrine 13:155 (2000).
Bergman, R.N., et al., Journal of Investigative Medicine 49:119 (2001).
Colditz, G.A., Medicine & Science in Sports & Exercise 31:S663 (1999).
Hall, W.D., et al., American Journal of the Medical Sciences 313:195 (1997).
Hall, J.E., et al., Annals of the New York Academy of Sciences 892:91 (1999).
Lepor, N.E., et al., American Journal of Cardiology 86:107 (2000).
Kernan, W.N., et al., New England J. Med. 343:1826 (2000).
Oparil, S., et al., Circulation 95:1301 (1997).
Turner, R., et al., Diabetes 44:1 (1995).
Tofovic, S.P., et al., Renal Failure 22:387 (2000).
Ball, P., et al., Endocrinology 113:1781 (1983).
Dubey, R.K., et al., Hypertension 31:522 (1998).
Dubey, R.K., et al., Biochem. Biophys. Res. Commun. 278:27 (2000).
Dubey, R.K., et al., Am. J. Physiol. Renal Physiol. 280:F365 (2001).
Dubey, R.K., et al., J. Appl. Physiol. 91:1868 (2001).
Dubey, R.K., et al., Hypertention 37:640 (2001).
Dubey, R.D., et al., Circ. Res. 84:229 (1999).
Gupta, M., et al., J. Steriod Biochem. Molec. Biol. 67:413 (1998).
Harris, R.B., Annu. Rev. Nutr. 20:45 (2000).
Liu, D., et al., J. Pharmacol Exp. Ther. 286:561 (1998).
Schwartz, M.W., et al., Nature 404:661 (2000).
Xiao, S., et al., Hypertension 37:645 (2001).
Zacharia, L.C., Hypertension 37:658 (2001).
Zhang, Y., et al., Nature 372:425 (1994).
Dubey R.K., et al., Abstract, Hypertension, National Library of Medicine, No. 9453356, Jan. 1998.
Nadal, Angel, et al., The FASEB Journal 12:1341 (1998).

* cited by examiner

Primary Examiner—Barbara P. Badio
(74) Attorney, Agent, or Firm—The McCallum Law Firm, LLC

(57) ABSTRACT

Methods are provided for preventing or treating risk factors for cardiovascular disease in an individual, comprising administering a therapeutically effective amount of a composition comprising an estradiol metabolite to said individual. Such risk factors include obesity, the metabolic syndrome, diabetes mellitus, vascular disorders, and renal disorders. Preferred estradiol metabolites include 2-methoxyestradiol, 4-methoxyestradiol, 2-hydroxyestradiol, and 4-hydroxyestradiol or prodrugs thereof. The compositions may also be in the form of a controlled release formulation. Methods are also provided for use of estradiol metabolites to treat or prevent insulin resistance, vascular endothelial dysfunction, hyperlipidemia, hypertension, diabetic nephropathy, proteinuria and reducing leptin levels. In addition, the methods provide a method of stabilizing glucose levels. These treatments may be used in either gender because of their lack of a feminizing estrogenic effect.

1 Claim, 14 Drawing Sheets

ADMINISTRATION OF ESTRADIOL METABOLITES FOR THE TREATMENT OR PREVENTION OF OBESITY, METABOLIC SYNDROME, DIABETES, AND VASCULAR AND RENAL DISORDERS

RELATED APPLICATIONS

This application claims priority from U.S. Provisional Application No. 60/312,741 filed Aug. 17, 2001.

FIELD OF THE INVENTION

The present invention relates generally to methods and compositions for use in the prevention or treatment of risk factors for cardiovascular diseases such as obesity, metabolic syndrome, diabetes, and vascular and renal disorders. More particularly, the present invention relates to the use of estradiol metabolites with little estrogenic activity such as 2-hydroxyestradiol, 4-hydroxyestradiol, 2-methoxyestradiol and 4-methoxyestradiol, all of which may be delivered in a controlled release formulation for the prevention or treatment of such disorders.

BACKGROUND OF THE INVENTION

Obesity is pandemic and worsening in developed countries (see e.g., Mokdad, A. H., et al., *J. Am. Medical Assoc.* 284:1650 (2000), the disclosure of which is incorporated herein by reference). Obesity contributes importantly to the metabolic syndrome (see e.g., Grundy, S. M., *Endocrine* 13:155 (2000) (hereinafter, "Grundy, 2000"); Bergman, R. N., et al., *Journal of Investigative Medicine* 49:119 (2001) (hereinafter, "Bergman, 2001"), the disclosures of which are incorporated herein by reference), a disorder characterized by hypertension, insulin resistance and hyperlipidemia (Grundy, 2000; Bergman, 2001). The metabolic syndrome in turn contributes to heart and vascular disease (see e.g., Colditz, G. A., *Medicine & Science in Sports & Exercise* 31:S663 (1999), the disclosure of which is incorporated herein by reference), and to the accelerating epidemic of end stage renal failure (see e.g., Hall, W. D, et al., *American Journal of the Medical Sciences* 313:195 (1997); Hall, J. E. et al., *Annals of the New York Academy of Sciences* 892:91 (1999), the disclosures of which are incorporated herein by reference). Unfortunately, pharmacological management of obesity has caused, rather than attenuated, cardiovascular disease. For example, a popular phentermine/fenfluramine combination produces valvular heart disease (see e.g., Lepor, N. E., et al., *American Journal of Cardiology* 86:107 (2000), the disclosure of which is incorporated herein by reference), while another popular treatment option, phenylpropanolamine, causes stroke (see e.g., Kernan, W. N., et al., *New England J. Med.* 343:1826 (2000), the disclosure of which is incorporated herein by reference). Thus, drugs that prevent or treat obesity and its metabolic, vascular and renal sequelae, without adversely affecting the heart, are badly needed.

Several compounds have been reported to cause a reduction in body weight. For example, Oparil, S., et al., *Circulation* 95:1301 (1997), the disclosure of which is incorporated herein by reference, reported that 17β-estradiol caused a reduction in body weight of rats as well as vascular protection. However, adverse effects to using 17β-estradiol are that undesirable feminizing effects are caused in males and there is increased risk of breast and uterine cancer in females due to the estrogenic effect of 17β-estradiol.

In that there appears to be a linkage between obesity, metabolic syndrome, diabetes, and vascular and renal disorders, it is important and desirable to be able to treat several or all of these conditions simultaneously with one pharmacological agent regardless of the gender of the individual.

SUMMARY OF THE INVENTION

Methods are provided for preventing or treating risk factors for cardiovascular disease in an individual, comprising administering a therapeutically effective amount of a composition comprising an estradiol metabolite to said individual. Such risk factors include obesity, the metabolic syndrome, diabetes mellitus, vascular disorders, and renal disorders. Preferred estradiol metabolites include 2-methoxyestradiol, 4-methoxyestradiol, 2-hydroxyestradiol, and 4-hydroxyestradiol or prodrugs thereof. The compositions may also be in the form of a controlled release formulation. Methods are also provided for use of estradiol metabolites to treat or prevent insulin resistance, vascular endothelial dysfunction, hyperlipidemia, hypertension, diabetic nephropathy and proteinuria. In addition, the methods provide a method of stabilizing glucose levels. These treatments may be used in either gender because of their lack of a feminizing estrogenic effect.

Other features and advantages of the invention will be apparent from the following description of the preferred embodiment, and from the claims

DETAILED DESCRIPTION OF THE INVENTION

I. Definitions

Figure 1:
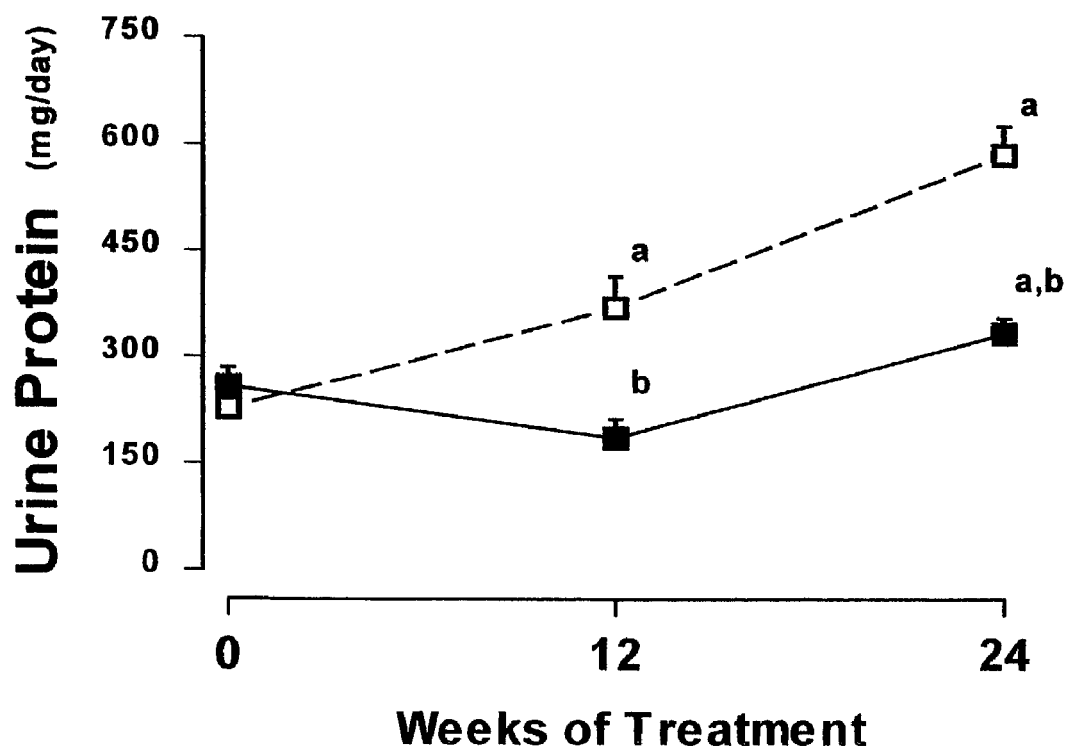
FIG. 1 shows urinary protein excretion in ZSF1 rats at baseline, 12 and 24 weeks into treatment with either vehicle (□) or 2-hydroxyestradiol (■). The symbol "a" indicates significantly different from baseline (within group), and the symbol "b" indicates significantly different from vehicle (between groups) (Fisher's Least Significant Difference test). 2-Factor analysis of variance indicated a significant ($p<0.001$) effect of time and treatment, as well as a significant ($p<0.001$) interaction between time and treatment. Values indicate means±SEM for 9 to 10 animals in each group.

The term "estradiol metabolite(s)" refers to metabolites of 17β-estradiol such as catecholestradiols and methoxyestradiols which exert little estrogenic activity and have a low affinity for the estrogen receptor, examples of which include 2-methoxyestradiol, 4-methoxyestradiol, 2-hydroxyestradiol and 4-hydroxyestradiol.

"Biodegradable" refers to polymers that dissolve or degrade in vivo within a period of time that is acceptable in a particular therapeutic situation. This time is typically less than five years and usually less than one year after exposure to a physiological pH and temperature, such as a pH ranging from 6 to 9 and a temperature ranging from 25° C. to 40° C.

The term "individual" refers to either a human or animal of the male or female gender.

The term "prodrug" refers to a compound that releases an estradiol metabolite.

The term "obesity" refers to a condition in which an individual has a body mass index greater than 25. Body mass index is defined as weight of the individual (expressed in kilograms) divided by the square of the height of the individual (expressed in meters).

"Metabolic syndrome" refers to a condition characterized by any or all of glucose intolerance, hyperinsulinemia, insulin resistance, hyperlipidemia, hypertension and obesity. Usually the metabolic syndrome is more prevalent in individuals who are also obese.

"Diabetes mellitus" refers to a disease process derived from multiple causative factors and characterized by elevated levels of plasma glucose or hyperglycemia in the fasting state or after administration of glucose during an oral glucose tolerance test.

The term "renal disorder" refers to an abnormality in the structure or function of the kidneys. Renal disorders may be characterized by nephropathy as evidenced by proteinuria, abnormal renal histopathology, such as glomerulosclerosis and severe tubulointerstitial and vascular changes, or reduced glomerular filtration rate.

"Insulin resistant" or "insulin resistance" refers to a decrease in an individual in the biological action of insulin in vivo as assessed by the rate of disposal of glucose from the bloodstream (e.g., into insulin-sensitive tissue, such as muscle, fat and liver). This assessment is evaluated clinically by an assessment of tolerance to a glucose challenge either orally or via the intravenous route (e.g., as described in Turner, R., et al., *Diabetes* 44:1 (1995), the disclosure of which is incorporated herein by reference). Individuals with Type II diabetes mellitus are "insulin resistant."

II. Methods

The following detailed description contains numerous specific details in order to provide a more thorough understanding of the elements that are relevant for a clear understanding of the invention, while eliminating, for the purposes of clarity, other elements that may be well known. Those of ordinary skill in the art will recognize that other elements are desirable and/or required in order to implement the present invention. However, because such elements are well known in the art, and because they do not facilitate a better understanding of the present invention, a discussion of such elements is not provided. The detailed description is provided hereinbelow with reference to the attached drawings.

The present invention provides methods of using estradiol metabolites to treat a wide variety of health conditions. In particular, the present invention provides methods for preventing or treating risk factors for cardiovascular diseases such as obesity, metabolic syndrome, diabetes, vascular disorders and renal disorders. The invention also specifically provides methods of administering to an individual a therapeutically effective amount of an estradiol metabolite for the prevention or treatment of obesity, the metabolic syndrome, diabetes mellitus, vascular disease or renal disease. Estradiol metabolites used to carry out the methods of the present invention include metabolites of 17β-estradiol such as catecholestradiols and methoxyestradiols which exert little estrogenic activity and have low affinity for the estrogen receptor, examples of which include 2-methoxyestradiol, 4-methoxyestradiol, 2-hydroxyestradiol and 4-hydroxyestradiol as well as others. Such estradiol metabolites may be incorporated in a controlled release formulation. Such estradiol metabolites may also be released from prodrugs.

The present invention also provides methods of administering to an individual a therapeutically effective amount of an estradiol metabolite for the prevention or treatment of insulin resistance, vascular endothelial dysfunction, hyperlipidemia, hypertension, diabetic nephropathy, or proteinuria. In accordance with the present invention, it has been found that such hyperlipidemia is hypercholesterolemia. Estradiol metabolites may also be incorporated in a controlled release formulation to practice the methods of the present invention. Such metabolites may further be released from prodrugs.

The present invention also provides methods of administering an estradiol metabolite in order to control glucose levels of an individual. Administration of such estradiol metabolites decreases polyuria, polydipsia or glycated hemoglobin levels. It has been further found that such estradiol metabolites improve oral glucose tolerance and may be administered in a controlled release formulation. Such estradiol metabolites may also be released from prodrugs.

The present invention further provides for administration of the estradiol metabolites to an individual in a controlled release formulation. In particular, the estradiol metabolites can be incorporated into biodegradable microparticles, biodegradable nanoparticles, patches, crystals, gels, hydrogels or liposomes and the like to carry out the methods of the present invention. The estradiol metabolites can also be incorporated into implants, vaginal rings, osmotic pumps, diffusion devices or transdermal delivery devices.

Biodegradable microparticles or nanoparticles used in a controlled release formulation include one or more polymers such as poly(lactide)s, poly(glycolide)s, poly(lactide-co-glycolide)s, poly(lactic acid)s, poly(glycolic acid)s, poly(lactic acid-co-glycolic acid)s, polycaprolactone, polycarbonates, polyesteramides, polyanhydrides, poly(amino acids), polyorthoesters, polyacetyls, polycyanoacrylates, polyetheresters, poly(dioxanone)s, poly(alkylene alkylate)s, copolymers of polyethylene glycol and polyorthoester, biodegradable polyurethanes, and blends and copolymers thereof.

Estradiol Metabolites

Estradiol metabolites used in accordance with the present invention include catecholestradiols such as 2-hydroxyestradiol (estra-1,3,5 (10)-triene-2,3,1 7-triol (17β)) or 4-hydroxyestradiol (estra-1,3,5 (10)-triene-3,4, 17-triol (17β)) or methoxyestradiols, such as 2-methoxyestradiol (estra-1,3,5 (10)-triene-2-methoxy-3,17-diol (17β)) or 4-methoxyestradiol (estra-1,3,5 (10)-triene-4-methoxy-3,17-diol (17β)). Commercial preparations of all of these compounds are readily available.

Estradiol metabolites may also be incorporated into a controlled release formulation. Such controlled release formulations may be biodegradable microparticles, biodegradable nanoparticles, patches, crystals, gels, hydrogels, liposomes, and the like. In addition, the estradiol metabolites may be incorporated into devices, such as implants, vaginal rings, osmotic pumps, diffusion devices and transdermal delivery devices. According to the present invention prodrugs of estradiol metabolites may also be used. Specific examples include esters of hydroxyestradiols and methoxyestradiols.

It will be apparent to the skilled artisan that the compounds listed above are exemplary only and that many variations may be used, depending on the particular hydroxylation or methylation site on the parent estradiol compound. For example, estradiol can be hydroxylated or methylated at many sites and such variations are known in the art.

Modes of Administration

Therapeutic compositions of the present invention can be formulated in an excipient that the individual to be treated can tolerate. Examples of such excipients include water, saline, Ringer's solution, dextrose solution, Hank's solution, and other physiologically balanced salt solutions. Nonaqueous vehicles, such as fixed oils, sesame oil, ethyl oleate, or triglycerides may also be used. Other useful formulations include suspensions containing viscosity enhancing agents, such as sodium carboxymethylcellulose, sorbitol, or dextran. Excipients can also contain minor amounts of additives, such as substances that enhance isotonicity and chemical stability.

Examples of buffers for use in formulations for the therapeutic compositions of the present invention include phosphate buffer, bicarbonate buffer and Tris buffer, while examples of preservatives include thimerosal, cresols, formalin and benzyl alcohol. Standard formulations can either be liquid injectables or solids which can be taken up in a suitable liquid as a suspension or solution for injection. Thus, in a non-liquid formulation, the excipient can comprise dextrose, human serum albumin, preservatives, etc., to which sterile water or saline is added prior to administration.

The present invention also has the objective of providing suitable topical, oral, systemic and parenteral formulations of the pharmaceutical compounds herein provided. The formulations can be administered in a wide variety of therapeutic dosage forms in conventional vehicles for administration. For example, the compounds can be formulated for oral administration in the form of tablets, capsules (each including timed release and sustained release formulations), pills, powders, granules, elixirs, tinctures, solutions, suspensions, syrups and emulsions. Likewise, they may also be administered intravenously (both bolus and infusion), during angioplasty/catheterization, intraperitoneally, subcutaneously, topically with or without occlusion, or intramuscularly, all using formulations well known to those of ordinary skill in the pharmaceutical arts.

Therapeutic compositions according to the present invention include a carrier. Carriers include compounds that increase the half-life of a therapeutic composition in the treated individual. Suitable carriers include, but are not limited to, polymeric controlled release vehicles, biodegradable implants, liposomes, bacteria, viruses, other cells and glycols.

Controlled Release Formulations

The method of the present invention can also employ controlled release formulations that are capable of slowly releasing a composition of the present invention into an individual. As used herein, a controlled release formulation can include a composition of the present invention in a controlled release vehicle. Such controlled release formulations are well known in the art. Suitable controlled release formulations include, but are not limited to, biocompatible polymers, other polymeric matrices, capsules, microcapsules, microparticles, nanoparticules, patches (see, U.S. Pat. Nos. 6,238,284; and 5,736,154, the disclosures of which are incorporated herein by reference), crystals (see, U.S. Pat. No. 5,827,531, the disclosure of which is incorporated herein by reference), bolus preparations, liposomes (see, U.S. Pat. Nos. 6,339,069; and 6,143,716, the disclosures of which are incorporated herein by reference), lipospheres, gels (see, U.S. Pat. No. 5,830,506, the disclosure of which is incorporated herein by reference), and hydrogels (see, U.S. Pat. Nos. 6,372,813; 6,372,248; and 6,367,929, the disclosures of which are incorporated herein by reference). Such controlled release vehicles also include devices, such as vaginal rings (see, U.S. Pat. Nos. 6,103,256; and 5,788,980, the disclosures of which are incorporated herein by reference), implants (see, U.S. Pat. Nos. 6,251,418; and 5,874,098, the disclosures of which are incorporated herein by reference), osmotic pumps, diffusion devices, and transdermal delivery systems. Other controlled release formulations of the present invention include liquids that, upon administration to an individual, form a solid or a gel in situ. Preferred controlled release formulations are biodegradable. All such compositions are well known in the art.

A preferred controlled release formulation of the present invention is capable of releasing a composition of the present invention into an individual at a constant rate sufficient to attain therapeutic dose levels of the composition. The therapeutic composition is preferably released over a period of time ranging from 1 day to about 12 months. More preferably, such a therapeutic composition is released over a 2,3,4,5,6,7 day through a 30 day time period.

Dosage

Acceptable protocols to administer therapeutic compositions of the present invention in an effective manner include individual dose size, number of doses, frequency of dose administration, and mode of administration. Determination of such protocols can be accomplished by those skilled in the art. A suitable single dose is capable of protecting (i.e. preventing or treating) an individual from disease when administered one or more times over a suitable time period. The need for additional administrations of a therapeutic composition can be determined by one of skill in the art in accordance with the given condition of a patient.

Prevention or Treatment of Health Conditions

It has been estimated that 60% of all Americans have a body mass index greater than 25. However, obesity is not just a problem for humans. Many animals also suffer adverse consequences related to obesity. For example, approximately 10 to 40% of cats and 25 to 50% of dogs receiving veterinary care have been reported to be overweight. Factors contributing to obesity include a sedentary lifestyle, confinement to indoors, and neutering. Obese animals have a greater risk for certain diseases including osteoarthritis, ligament injuries, perineal dermatitis, diabetes mellitus, cardiomyopathy, and urologic syndromes. Therefore, it is critical to maintain a healthy weight in order to minimize disease risk. See, U.S. Pat. No. 6,071,544, the disclosure of which is incorporated herein by reference.

The present invention provides methods of administering to an individual a therapeutically effective amount of an estradiol metabolite to prevent or treat obesity. Such estradiol metabolites may be incorporated in a controlled release formulation and may also be administered as a prodrug.

The present invention also provides methods of administering to an individual a therapeutically effective amount of an estradiol metabolite to prevent or treat the metabolic syndrome. The present invention further provides that such estradiol metabolites may be administered to an individual with the metabolic syndrome to prevent the onset of diabetes mellitus, renal disease, glucose intolerance, hyperinsulinemia, insulin resistance, hyperlipidemia, hypertension and obesity. In another embodiment, such estradiol metabolites may be administered to an individual with the metabolic syndrome to treat diabetes mellitus, renal disease, glucose intolerance, hyperinsulinemia, insulin resistance, hyperlipidemia, hypertension and obesity. In one embodiment of the present invention, such estradiol metabolites can be administered to an individual to prevent or treat hypercholesterolemia. In an alternate embodiment, such estradiol metabolites may be administered to an individual for the purpose of controlling glucose levels. This may be evidenced by a decrease in polyuria, polydipsia, and glycated hemoglobin levels. Additionally, there may also be an improvement in oral glucose tolerance. Such estradiol metabolites may be incorporated in a controlled release formulation or may also be administered as a prodrug.

Persistent or uncontrolled hyperglycemia is associated with increased and premature morbidity and mortality. Often abnormal glucose homeostasis is associated both directly and indirectly with alterations of the lipid, lipoprotein and apolipoprotein metabolism and other metabolic and hemodynamic disease. Therefore patients with Type II diabetes mellitus are at especially increased risk of macrovascular and microvascular complications, including coronary heart disease, stroke, peripheral vascular disease, hypertension, nephropathy, neuropathy, and retinopathy. Therefore, therapeutic control of glucose homeostasis, lipid metabolism and hypertension are critically important in the clinical management and treatment of diabetes mellitus.

Early intervention in individuals at risk to develop Type II diabetes mellitus, focusing on reducing the pathological hyperglycemia or impaired glucose tolerance, may prevent or delay the progression towards Type II diabetes mellitus and associated complications and/or metabolic syndrome. Therefore, by effectively treating impaired oral glucose tolerance and/or elevated blood glucose levels, one can prevent or inhibit the progression of the disorder to Type II diabetes mellitus or the metabolic syndrome.

The present invention further provides methods of administering to an individual a therapeutically effective amount of an estradiol metabolite to prevent or treat diabetes mellitus. Alternatively, such estradiol metabolites may be administered to an individual at risk of developing diabetes mellitus. Such individual may demonstrate hyperglycemia or impaired glucose tolerance and administration of estradiol metabolites according to the present methods will work to control glucose levels. Alternatively, such estradiol metabolites may be administered to an individual with Type II diabetes to prevent or treat peripheral vascular disease, hypertension, nephropathy, neuropathy and retinopathy. Estradiol metabolites may be administered to an individual with Type II diabetes in order to control glucose levels. Administration of such estradiol metabolites may decrease polyuria, polydipsia and glycated hemoglobin levels. It may also increase oral glucose tolerance. All such estradiol metabolites may be incorporated in a controlled release formulation or may be administered as a prodrug.

The present invention also provides methods of administering to an individual a therapeutically effective amount of an estradiol metabolite to prevent or treat renal disease. In alternative embodiments, such estradiol metabolite may be administered to an individual with the metabolic syndrome to prevent the onset of renal disease. Estradiol metabolites may also be administered an individual to prevent or treat diabetic nephropathy to improve vascular endothelial function. Estradiol metabolites may also be administered to prevent or treat proteinuria. All such estradiol metabolites may be incorporated in a controlled release formulation or may also be administered as a prodrug.

The present invention also provides methods of administering to an individual a therapeutically effective amount of an estradiol metabolite to prevent or treat insulin resistance. Such estradiol metabolites can be administered to an individual with Type II diabetes. Alternatively, such estradiol metabolites can be administered to an individual at risk of developing Type II diabetes. Such estradiol metabolites can also be administered to an individual with the metabolic syndrome. Alternately, such estradiol metabolites can be administered to an individual at risk of developing the metabolic syndrome. All such estradiol metabolites may be incorporated in a controlled release formulation or may be administered as a prodrug.

The present invention will now be further illustrated, but is by no means limited to, the following examples. It will be apparent to those skilled in the art that the techniques described in the examples represent techniques discovered by the inventors to function well in the practice of the invention, and thus can be considered to constitute presently preferred modes for its practice. However, it should be apparent to those of skill in the art that many modifications, both to materials and methods may be made in the specific embodiments without departing from the spirit and scope of this invention.

EXAMPLES

Example 1

Treatment of Male ZSF1 Rats for 26 Weeks with 2-hydroxyestradiol to Assess the Anti-Obesity, Anti-Diabetic, Cholesterol Lowering and Renal Effects.

Creation of Rat Model

Twenty 12-week-old male obese ZSF1 rats (Genetic Models Inc., Indianapolis, Ind.) were used. Obese ZSF1 rats were developed by crossing lean female Zucker Diabetic Fatty rats (ZDF +/fa) and lean male Spontaneously Hypertensive Heart Failure rats (SHHF/Mcc-fa$^{cp}$, +/cp). As recently described by Tofovic, S. P., et al., *Renal Failure* 22: 387 (2000) the disclosure of which is incorporated herein by reference, compared with several different rat strains including Wistar-Kyoto normotensive rats, spontaneously hypertensive rats and obese SHHF/Mcc-fa$^{cp}$ rats, obese ZSF1 rats have the metabolic syndrome (i.e., hypertension, diabetes and hyperlipidemia), left ventricular dysfunction, and develop nephropathy as characterized by massive proteinuria, abnormal renal histopathology (glomerulosclerosis and severe tubulointerstitial and vascular changes) and reduced glomerular filtration rate. Thus, this rat strain develops obesity, the metabolic syndrome and the end-organ sequelae associated with the metabolic syndrome.

Animal Experimentation

At baseline, animals were placed in metabolic cages and food intake, water intake, urine output and urinary excretion of proteins (bicinchoninic acid method) and glucose (Infinity™ Glucose Reagent, Sigma Diagnostics, St Louis, Mo.) were determined. Next, osmotic mini pumps infusing either vehicle (polyethylene glycol 400, 2.5 ul/hour) or 2-hydroxyestradiol (10 ug/kg/hour) were implanted subcutaneously (random assignment). Minipumps were replaced every 33 days. Metabolic cage studies were repeated 12 and 24 weeks after initiation of treatments. After 9 and 25 weeks of treatment, animals were fasted overnight, and blood samples (tail vein) for measurement of cholesterol were taken. Plasma samples were analyzed in duplicates for cholesterol levels (Sigma Diagnostics, St. Louis, Mo.). After 26 weeks of treatment, animals were fasted overnight, an oral glucose tolerance test was conducted and total glycated hemoglobin levels were determined (Sigma Diagnostics). Plasma glucose levels were measured with the Precision Q.I.D. Blood Glucose Test Strips kit (Medisense, Inc., Bedford, Mass.).

After 26 weeks of treatment, animals were anesthetized and instrumented for assessment of heart performance, renal hemodynamics and mesenteric vascular reactivity. A PE-50 catheter was advanced via the carotid artery into the left ventricle and connected to a heart-performance analyzer (Micro-Med, Inc., Louisville, Ky.) for continuous measurement of ten time/pressure variables. A PE-50 catheter was inserted into the femoral artery and connected to a blood pressure analyzer (Micro-Med, Inc.) for measurement of arterial blood pressure. A PE-10 catheter was inserted into the left ureter for urine collection, and a flow probe (Transonic Systems, Inc., Ithaca, N.Y.) was placed on the left renal artery for determination of renal blood flow. An infusion of $^{14}$C-inulin (0.035 uCi/20 ul saline/min) was initiated, and after 60 minutes, two 30-minute clearance periods were conducted. A mid-point blood sample (300 ul) for measurement of radioactivity was collected. Plasma and urine $^{14}$C-inulin radioactivity were measured, and renal clearance of $^{14}$C-inulin was calculated. A flow probe was placed on the mesenteric artery for determination of mesenteric blood flow, and a 32-gauge needle was inserted into the mesenteric artery and attached to a Y-connector for dual intramesenteric artery infusions (25 ul/min each). Angiotensin II (30 ng/min) plus methoxamine (3 ug/min) was delivered via one intramesenteric artery infusion line into the mesenteric vascular bed to the mesenteric vascular bed. Next, vascular responses to increasing doses of acetylcholine (0.3, 1.0 and 3.0 ug/min, 5 minutes per dose) and sodium nitroprusside (0.5, 1.5 and 5.0 ug/min, 5 minutes per dose) were elicited by infusing these agents via the other intramesenteric artery infusion line into the mesenteric vascular bed. Vascular resistances were calculated as arterial blood pressure divided by blood flow.

Statistical Analysis

All values refer to means±SEM for 9 to 10 animals in each group. Statistical significance was calculated using either an unpaired Student's t-test or a 2-factor analysis of variance (repeated measures) followed by a Fisher's Least Significance Difference test if appropriate. The criterion of significance was p<0.05.

Results

At baseline, control and 2-hydroxyestradiol groups weighed 484±4 and 483±9 grams, respectively. Body weight was lower (P<0.001) in 2-hydroxyestradiol-treated rats after 12 and 26 weeks of treatment (611±9 versus 545±13 grams at 12 weeks and 768±14 versus 571±13 grams at 26 weeks in control versus 2-hydroxyestradiol-treated rats, respectively). At baseline, control and 2-hydroxyestradiol groups had similar food intakes (41.4±1.6 and 43.9±1.4 grams/day, respectively). Food intake was lower (P<0.001) in 2-hydroxyestradiol rats after 12 and 24 weeks of treatment (35.2±1.9 versus 26.4±1.3 grams/day at 12 weeks and 44.6±1.0 versus 36.6±0.9 grams/day at 24 weeks in control versus 2-hydroxyestradiol treated rats, respectively).

At baseline, both groups exhibited glucosuria (9.8±0.2 and 8.5±1.0 grams glucose/day for the control and 2-hydroxyestradiol groups, respectively). Glucosuria was reduced (P<0.001) by 12 and 24 weeks of treatment with 2-hydroxyestradiol (5.5±0.8 versus 0.2±0.2 grams glucose/day at 12 weeks and 6.5±0.4 versus 1.7±0.5 grams glucose/day at 24 weeks in control versus 2-hydroxyestradiol-treated rats, respectively). Also, treatment for 26 weeks with 2-hydroxyestradiol improved (P<0.01) the oral glucose tolerance test (plasma glucose 2 hours after an oral dose of 2 grams of glucose per kg body weight was 326±12 versus 265±13 mg/100 ml in control versus 2-hydroxyestradiol-treated rats, respectively). Moreover, 26 weeks into the study, glycated hemoglobin (a time-averaged index of glucose control) was 12.5±1.7% versus 3.8±0.7% in control versus 2-hydroxyestradiol-treated rats, respectively (P<0.001). At baseline, both groups exhibited polyuria (94.8±8.2 and 102±9.2 mls of urine/day for control and 2-hydroxyestradiol groups, respectively) and polydipsia (115±10 and 135±10 mls of water consumed/day for the control and 2-hydroxyestradiol groups, respectively). Polyuria was reduced (P<0.001) by 12 and 24 weeks of treatment with 2-hydroxyestradiol (57.6±7.5 versus 23.6±2.4 mls of urine/day at 12 weeks and 86.5±3.0 versus 45.6±3.8 mls of urine/day at 24 weeks in control versus 2-hydroxyestradiol-treated rats, respectively). Polydipsia also was reduced (P<0.001) by 12 and 24 weeks of treatment with 2-hydroxyestradiol (67.0±7.2 versus 40.1±4.0 mls of water consumed/day at 12 weeks and 131.8±7.0 versus 67.4±4.5 mls of water consumed at 24 weeks in control versus 2-hydroxyestradiol-treated rats, respectively).

Treatment with 2-hydroxyestradiol reduced (P<0.001) hypercholesterolemia (205±11 versus 151±9 mg cholesterol/100 ml at 9 weeks and 399±24 versus 247±28 mg cholesterol/100 ml at 25 weeks in control versus 2-hydroxyestradiol-treated rats, respectively).

Treatment with 2-hydroxyestradiol for 26 weeks reduced (P<0.05) mean arterial blood pressure (133±6 versus 122±5 mm Hg in control versus 2-hydroxyestradiol-treated rats, respectively). Although treatment for 26 weeks with 2-hydroxyestradiol did not affect renal blood flow, renal vascular resistance or glomerular filtration rate (as shown in Table 1 below), 2-hydroxyestradiol did have a striking effect on urinary protein excretion. At baseline (12 weeks-of-age), control animals excreted large amounts of protein (227±29 mg protein/day) and proteinuria continued to increase with aging (P<0.001). Importantly, 2-hydroxyestradiol significantly (P<0.001) attenuated the progression of proteinuria (FIG. 1).

TABLE 1

Body weight, food intake, metabolic parameters and renal parameters in control versus 2-hydroxyestradiol-treated ZDF1 rats after approximately 6 months of treatment.

| Parameter | Control | 2-Hydroxyestradiol |
| --- | --- | --- |
| Body Weight (grams) | 768 ± 14 | 571 ± 11 (P < 0.001) |
| Food Intake (grams) | 44.6 ± 1.0 | 36.6 ± 0.9 (P < 0.001) |
| Urinary Glucose Excretion (grams/day) | 6.5 ± 0.4 | 1.7 ± 0.5 (P < 0.001) |
| Plasma Glucose 2 Hours After Oral Glucose Load of 2 g/kg (mg/100 ml) | 326 ± 12 | 265 ± 13 (P < 0.01) |
| Glycated Hemoglobin (%) | 12.5 ± 1.7 | 3.8 ± 0.7% (P < 0.001) |
| Urine Volume (ml/day) | 86.5 ± 3.0 | 45.6 ± 3.8 (P < 0.001) |
| Water Intake (ml/day) | 131.8 ± 7.0 | 67.4 ± 4.5 (P < 0.001) |
| Plasma Cholesterol (mg/100 ml) | 399 ± 24 | 247 ± 28 (P < 0.001) |
| Urinary Protein Excretion (mg/day) | 586 ± 41 | 333 ± 21 (P < 0.001) |
| Renal Blood Flow (ml/min/gram kidney) | 3.6 ± 0.6 | 3.3 ± 0.6 |
| Renal Vascular Resistance (mm Hg/ml/min/gram kidney) | 44 ± 6 | 42 ± 7 |
| Glomerular Filtration Rate (ml/min/gram kidney) | 0.84 ± 0.08 | 0.76 ± 0.09 |

Values represent means ± SEM for 9–10 rats in each group. P-values were calculated with an unpaired Student's t-test.

Figure 2:
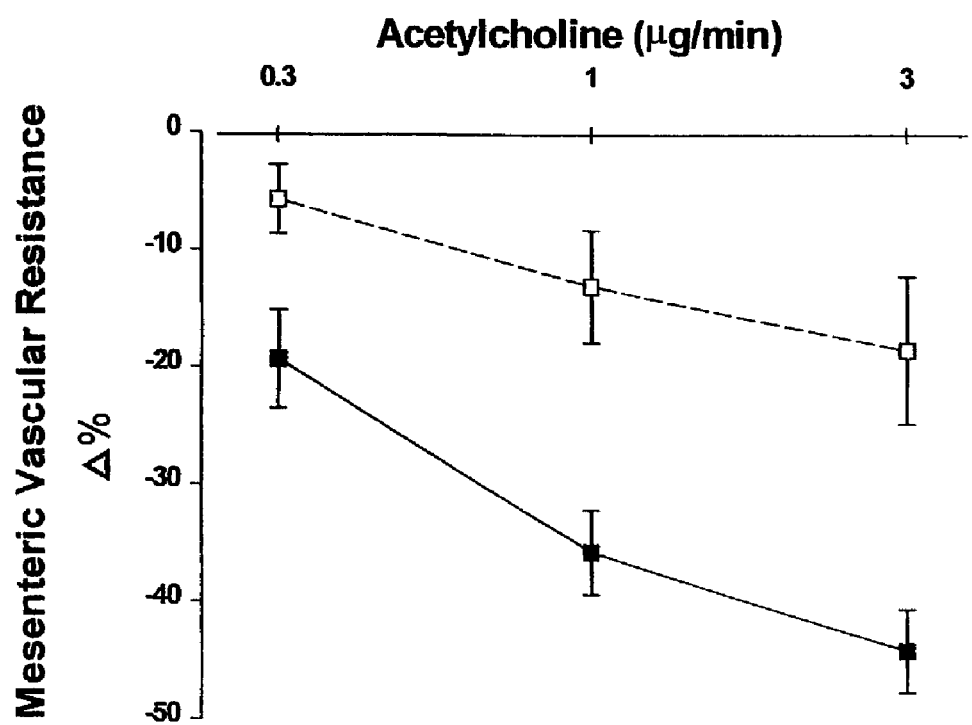
FIG. 2 shows effects of acetylcholine on mesenteric vascular resistance in ZSF1 rats 26 weeks into treatment with either vehicle (□) or 2-hydroxyestradiol (■). 2-Factor analysis of variance indicated a significant effect of 2-hydroxyestradiol on responses to acetylcholine ($P<0.006$). Values indicate means±SEM for 9 to 10 animals in each group.
Figure 3:
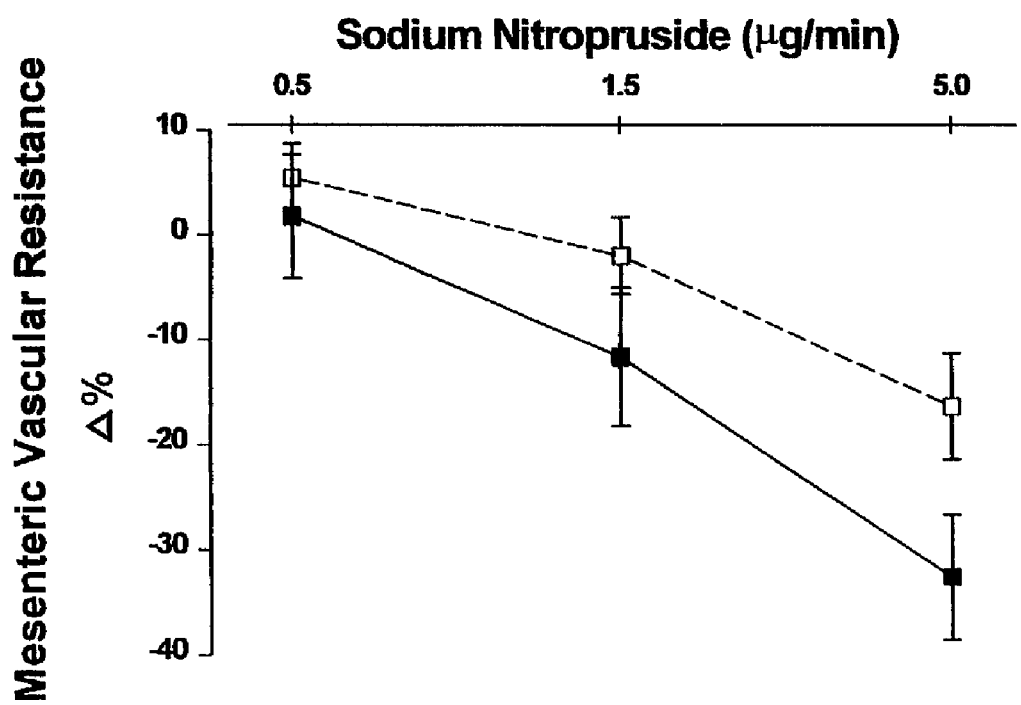
FIG. 3 shows effects of sodium nitroprusside on mesenteric vascular resistance in ZSF1 rats 26 weeks into treatment with either vehicle (□) or 2-hydroxyestradiol (■). 2-Factor analysis of variance indicated a non-significant effect of 2-hydroxyestradiol on responses to sodium nitroprusside ($p<0.201$). Values indicate means±SEM for 9 to 10 animals in each group.

At 26 weeks into the treatments, vasodilator responses in the mesentery were assessed. The decreases in mesenteric vascular resistance induced by acetylcholine were greater in 2-hydroxyestradiol-treated rats compared with control rats (FIG. 2). 2-Hydroxyestradiol only slightly (non-significantly) enhanced vasodilation induced by sodium nitroprusside (FIG. 3) indicating that the enhancement of responses to acetylcholine was mediated mostly by increased release of endothelial-dependent relaxing factors.

There were no effects of chronic treatment (26 weeks) with 2-hydroxyestradiol on heart performance in situ. No differences were detected between treated and control groups with regard to indices of ventricular diastolic or systolic function including heart rate, ventricular peak systolic pressure, rate of maximal change in pressure during ventricular contraction, rate of maximal change in pressure during ventricular relaxation, ventricular end diastolic pressure, ventricular diastolic minimal pressure, duration of ventricular contraction, duration of ventricular relaxation, time to ½ ventricular relaxation, time constant for ventricular relaxation or heart rate pressure product (as shown in Table 2 below).

TABLE 2

Hemodynamic parameters and cardiac performance parameters in control versus 2-hydroxyestradiol-treated ZDF1 rats after approximately 6 months of treatment.

| Parameter | Control | 2-Hydroxyestradiol |
|---|---|---|
| Mean Blood Pressure (mm Hg) | 133 ± 6 | 122 ± 5 ($P < 0.05$) |
| Heart Rate (beats/min) | 363 ± 4 | 352 ± 9 |
| Ventricular Peak Systolic Pressure (mm Hg) | 189 ± 5 | 172 ± 9 |
| $+dP/dt_{max}$ (mm Hg/sec) | 14,539 ± 692 | 11,805 ± 943 |
| $-dP/dt_{max}$ (mm Hg/sec) | 7633 ± 293 | 6853 ± 382 |
| Ventricular End Diastolic Pressure (mm Hg) | 3.0 ± 1.4 | 4.2 ± 1.0 |
| Ventricular Minimum Diastolic Pressure (mm Hg) | −2.7 ± 1.8 | −1.4 ± 1.1 |
| Duration of Contraction (msec) | 34.8 ± 2.7 | 38.8 ± 3.5 |
| Duration of Relaxation (msec) | 96.8 ± 4.3 | 96.3 ± 6.3 |
| Half-Time of Ventricular Relaxation (msec) | 49.1 ± 3.8 | 49.1 ± 3.6 |
| Time Constant of Ventricular Relaxation (msec) | 18.5 ± 2.9 | 16.7 ± 1.9 |
| Heart Rate × Ventricular Peak Systolic Pressure ([beats/min] × mm Hg) | 68,504 ± 2,267 | 60,949 ± 4,237 |
| $+dP/dt_{max}$/Ventricular Peak Systolic Pressure (1/sec) | 76.8 ± 2.6 | 69.9 ± 2.5 |

Values represent means ± SEM for 9–10 rats in each group. P-value was calculated with an unpaired Student's t-test.

Example 2

Treatment of Male and Female ZSF1 Rats for 24 Weeks with 2-hydroxyestradiol, or 2-methoxyestradiol to Assess the Anti-Obesity, Anti-Diabetic, Cholesterol Lowering and Renal Effects.

Experimental Design

Male ZSF1 rats were treated continuously for 24 weeks with polyethylene glycol 400 (PEG 400) (Sigma, St. Louis, Mo.) or one of three doses of 2-hydroxyestradiol or 2-methoxyestradiol (Steraloids, Inc. Newport, R.I.) dissolved in PEG 400. The three doses were 1 ug/kg/hr, 3 ug/kg/hr or 10 ug/kg/hr. Female ZSF1 rats were treated continuously for 24 weeks with either PEG 400 or 10 ug/kg/hr of 2-hydroxyestradiol. Female ZSF1 rats were ovarectomized at 11 weeks of age. For all animals, both male and female, treatments with estradiol metabolites were begun at approximately 13 weeks of age. One group of male ZSF1 rats received only PEG 400 but were pair fed to receive the same daily food intake as the male ZSF1 rats treated with 10 ug/kg/hr 2-hydroxyestradiol. Treatment was administered via subcutaneous implanted pumps (Alzet Osmotic Pump, Model 2ML4, Alza Corporation, Palo Alto, Calif.). The study was designed to evaluate treatment effects and dose responses on body weight, food intake, water intake, urine output, urinary protein excretion, cholesterol levels, plasma glucose levels and glucose tolerance.

Treatments

Stock solutions of both 2-hydroxyestradiol and 2-methoxyestradiol were made by dissolving the required amount of estradiol metabolite in PEG 400. This solution was diluted in PEG 400 to deliver the three required doses based on the mean weight of each treatment group and the stated volume delivery rate for each lot of osmotic pumps in the study. This stock solution was prepared fresh prior to each osmotic pump implantation in each group. The control solution of PEG 400 was created in the same manner.

Osmotic Minipumps

All treatments were administered via a subcutaneously implanted osmotic pump (Alzet Osmotic Pump, Model 2ML4, Alza Corporation, Palo Alto, Calif.). Each lot of osmotic pumps were delivered with the stated rate of delivery and formulation concentrations were adjusted to ensure delivery of 1,3, or 10 ug/kg/hr based on the stated rate of delivery of each lot. Doses were adjusted for the mean weight of the animals in the treatment group obtained 24 hours prior to implantation of the osmotic minipump.

Animals were anesthetized prior to implantation of an osmotic minipump with halothane and oxygen (2.5 liter/min) delivered by a Fluotec 3 anesthetic device (Ohmeda, Steeton, UK). After lightly anesthetizing each animal, implantation was accomplished by shaving the back and creating a half-inch incision in which to insert the osmotic minipump. The incision was then closed with wound clips that were removed in seven days. Osmotic minipumps were replaced at 33-day intervals and each time a particular animal received an osmotic minipump, the insertion point was changed.

Prior to implantation, osmotic minipumps were filled as directed in the manufacturer's instructions. Lot number and infusion rate for each lot was recorded. Once removed, osmotic minipumps were placed in appropriate containers and stored at −80° C. for future analysis.

Metabolic Cages

Metabolic cages (Nalgene, Rochester, N.Y.) were used in this study. Animals were placed in metabolic cages for 48 hours. The first 24-hour period was considered an acclimation period, while food and fluid intake and urine volume were measured during the second 24-hour period. Additionally, a tail vein sample was obtained to measure blood glucose, sodium, potassium, albumin and creatinine. The blood was further analyzed to assess creatinine clearance, fractional sodium excretion, fractional potassium excretion and fractional albumin excretion. In addition, the following criteria were also assessed while the animals were in the metabolic cages: body weight, feed intake, water intake, urine output, urinary protein, urinary albumin, urinary glucose, urinary sodium and urinary potassium.

Experimental Data Analysis

Body weights were assessed 24 hours before pump implantation and those weights were used to calculate the dosage of drug or vehicle to be given to each animal based on the mean body weight of each group. Animals were weighed approximately once every two months prior to being placed in a metabolic cage.

Food intake was measured by filling the food containers with standard powder laboratory food up to a total weight of 250 grams. Food containers were weighed again in 24-hours to assess food intake as calculated by the difference between the two weights.

Water intake was measured by filling labeled water bottles with water to the 250 ml mark. The water level was later assessed 24-hours later and the water intake calculated as the difference between the two measurements.

Urine volume was measured by collecting urine over a 24-hour period and weighing it.

Urinary protein excretion was measured by spectrophotometric assay using a bicinchoninic acid reagent (Pierce, Rockford, Ill.). 24-hour urinary protein excretion was calculated as a product of the 24-hour urine output and urinary protein concentration.

Urinary glucose excretion was measured by spectrophotometric assay using the Infinity™ Glucose Reagent (Sigma Diagnostics) as directed by the manufacturer's instructions. A 24-hour urinary glucose excretion was calculated as the product of 24-hour urine output and glucose concentration in urine.

Blood glucose was measured by collecting a drop of blood from a tail vein and placing it on a glucose test strip (Precision QID Blood Glucose Test Strips kit) and the result was read by Precision QID glucometer (Medisense, Inc.).

A response to the administration of oral glucose was obtained by fasting the animals for 16-hours and then collecting a drop of blood from the tail vein. Then each animal was given 2 gram/4 ml/kg water solution of oral glucose via oral gavage and blood was collected after 30, 60 and 120 minutes. Blood glucose levels were assessed as above.

Leptin levels were measured by a mouse leptin ELISA kit (Crystal Chem, Inc., Chicago, Ill.).

Glycated hemoglobin (HbA1c) levels were measured using the A1cNow™ monitor (Metrika, Sunnyvale, Calif.).

Results

Treatment of ZSF1 rats with 2-methoxyestradiol in Example 2 proved to have similar results as those found with 2-hydroxyestradiol in as described above in Example 1

Figure 4:
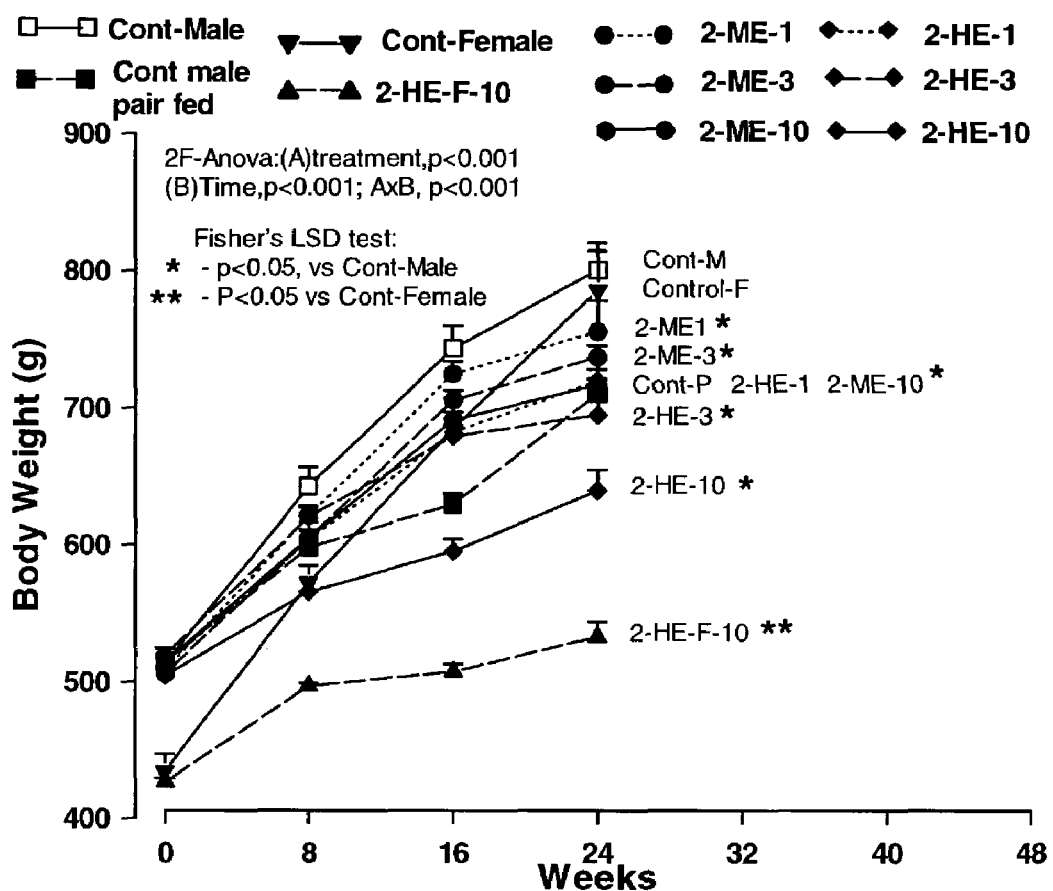
FIG. 4 shows effects of treatment with 1, 3 or 10 ug/kg/hr 2-hydroxyestradiol or 2-methoxyestradiol on weight gain in male or female ZSF1 rats over a 24-week period of time compared with untreated males ("Cont-M" or "Cont-Male"), untreated females ("Cont-F" or "Cont-Female") and untreated males pair fed to the 10 ug/kg/hr dose of 2-hydroxyestradiol ("Cont-P" or "contr male pair fed"). "2-HE-1", "2-HE-3" and "2-HE-10" indicate 1, 3 and 10 ug/kg 2-hydroxyestradiol, respectively, in males and "2-HE-F-10" indicates 10 ug/kg/hr 2-hydroxyestradiol in females. "2-ME- 1", "2-ME-3" and "2-ME-10" indicate 1, 3 and 10 ug/kg/hr 2-methoxyestradiol, respectively, in males.
Figure 5:
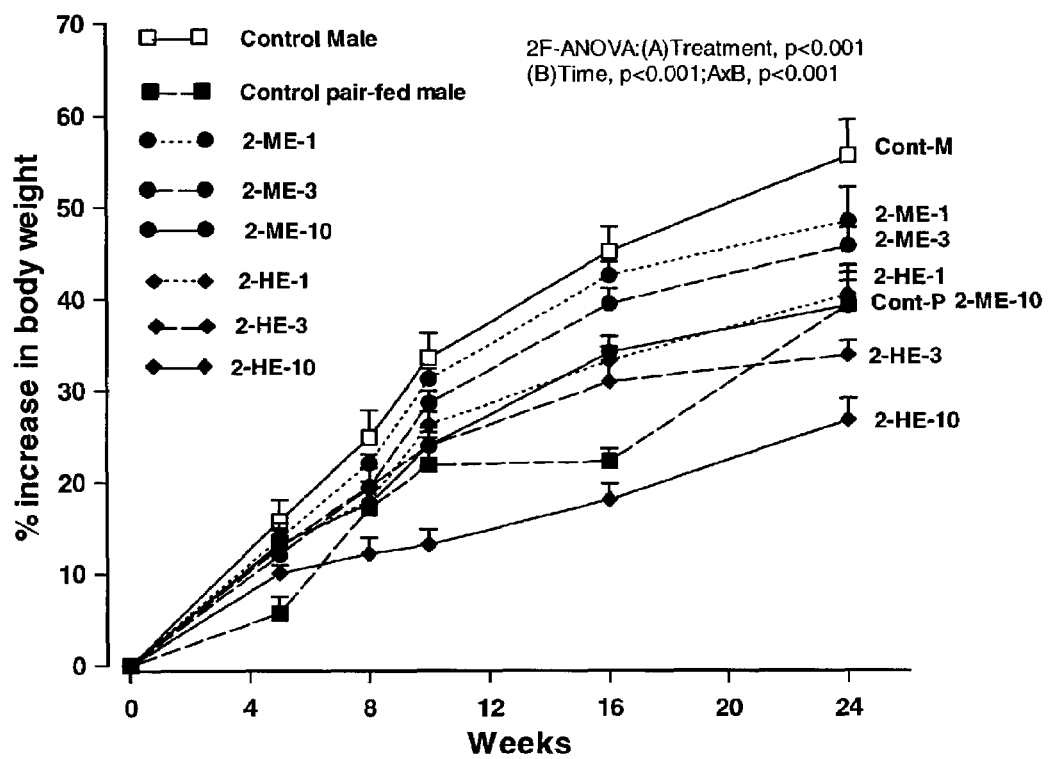
FIG. 5 shows effects of treatment with 1, 3 or 10 ug/kg/hr 2-hydroxyestradiol ("2-HE-1", "2-HE-3" and "2-HE-10", respectively) or 2-methoxyestradiol ("2-ME-1", "2-ME-3" and "2-ME-10", respectively) on percentage weight gain in male ZSF1 rats over a 24-week period of time compared with untreated males ("Cont-M" or "Control-Male") and untreated males pair fed to the 10 ug/kg/hr dose of 2-hydroxyestradiol ("Cont-P" or "Control pair-fed male").
Figure 6:
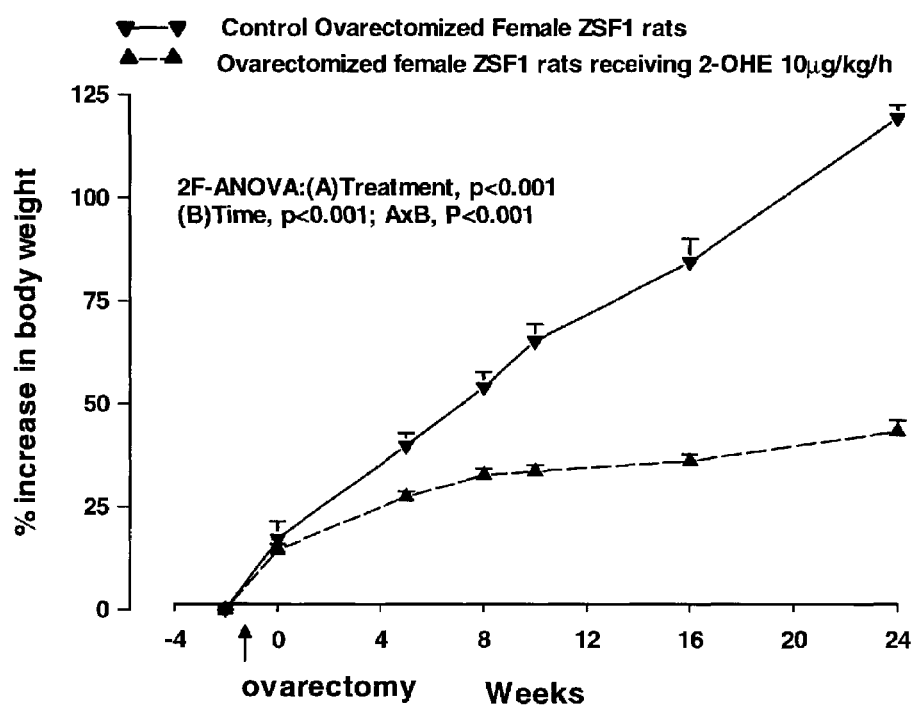
FIG. 6 shows effects of treatment with 10 ug/kg/hr 2-hydroxyestradiol on percentage increase in body weight in female ZSF1 rats over a 24-week period of time compared with untreated control females.

At baseline, there was no difference in the weight of treated or control groups of male animals (see FIG. 4). Treatment with either 2-methoxyestradiol or 2-hydroxyestradiol resulted in less body weight gain and lower food intake (see FIGS. 4 and 5). The same results were found in female treated animals after treatment with 10 ug/kg/hr 2-hydroxyestradiol (see FIG. 6).

Figure 7:
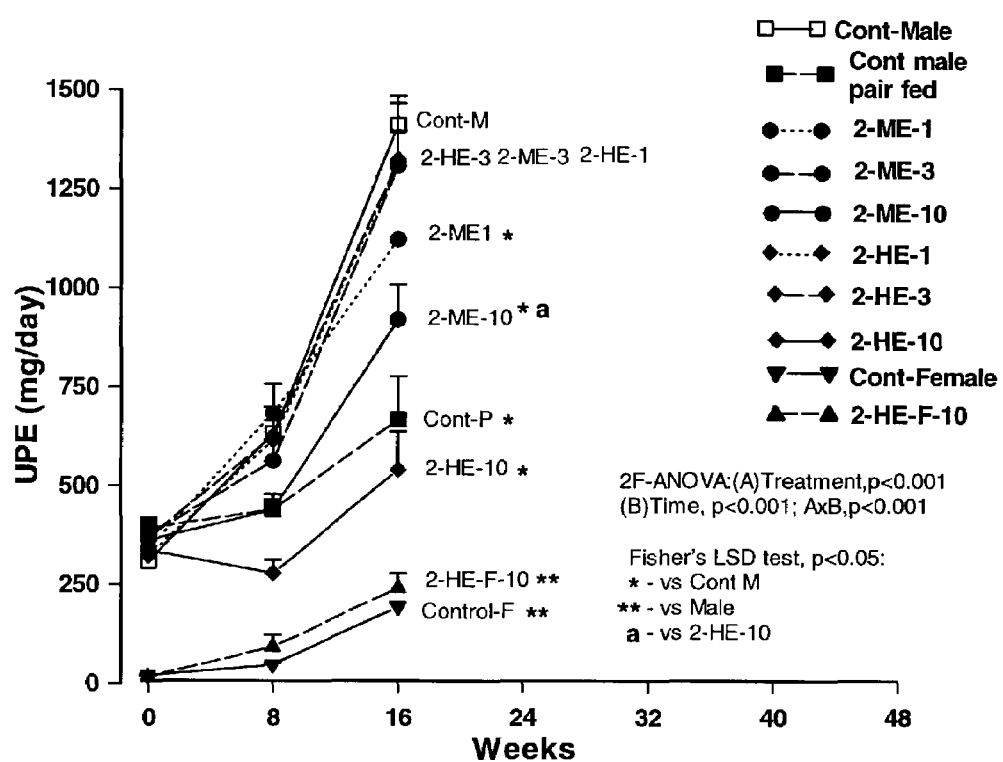
FIG. 7 shows effects of treatment with 1, 3 or 10 ug/kg/hr 2-hydroxyestradiol or 2-methoxyestradiol on urinary protein excretion ("UPE") in male or female ZSF1 rats over a 24-week period of time compared with untreated males ("Cont-M" or "Cont-Male"), untreated females ("Cont-F" or "Cont-Female") and untreated males pair fed to the 10 ug/kg/hr dose of 2-hydroxyestradiol ("Cont-P" or "contr male pair fed"). "2-HE-1", "2-HE-3" and "2-HE-10" indicate 1, 3 and 10 ug/kg/hr 2-hydroxyestradiol, respectively, in males and "2-HE-F-10" indicates 10 ug/kg/hr 2-hydroxyestradiol in females. "2-ME-1", "2-ME-3" and "2-ME-10" indicate 1, 3 and 10 ug/kg/hr 2-methoxyestradiol, respectively, in males.

Additionally, baseline urinary protein excretion was similar among all groups of male animals. After 24-weeks of treatment with 1, 3 or 10 ug/kg/hr 2-hydroxyestradiol or 2-methoxyestradiol, urinary protein excretion was lower in male animals treated with estradiol metabolites when compared to control animals (see FIG. 7). Female animals demonstrated lower initial levels of urinary protein excretion, hence there was little to improve upon with administration of estradiol metabolites. In addition, urinary protein excretion did not drastically increase in female animals.

Figure 8:
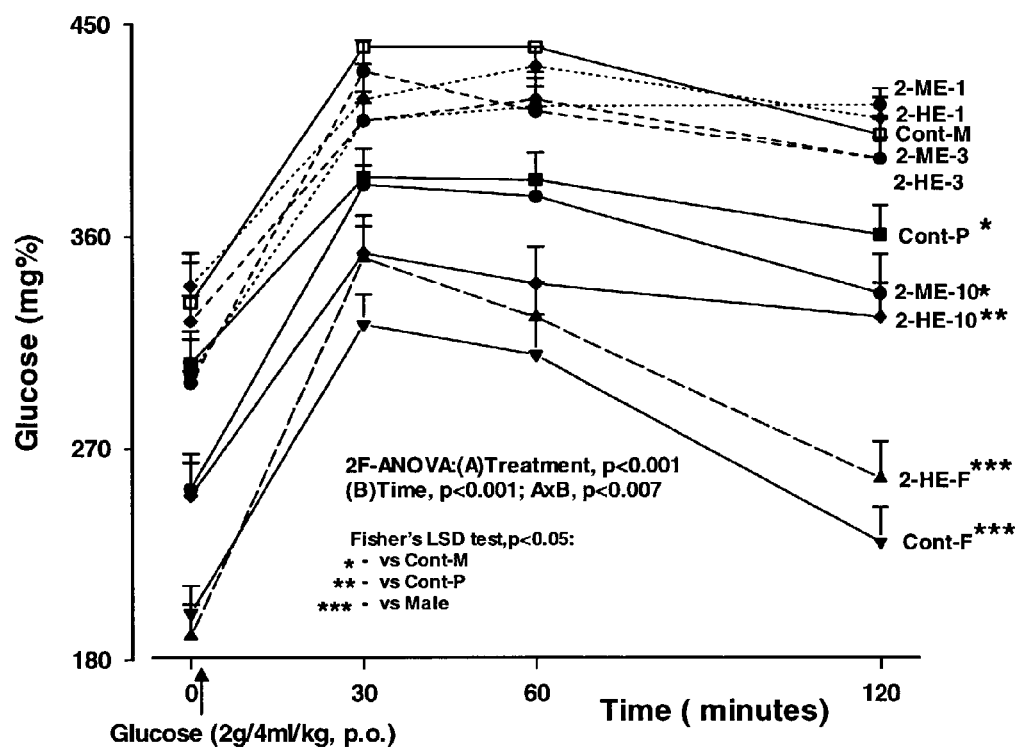
FIG. 8 shows effects of treatment with 1, 3 or 10 ug/kg/hr 2-hydroxyestradiol or 2-methoxyestradiol for 14 to 15 weeks on plasma glucose levels in an oral glucose tolerance test over 120 minutes in male or female ZSF1 rats compared with untreated males ("Cont-M"), untreated females ("Cont-F") and untreated males pair fed to the 10 ug/kg/hr dose of 2-hydroxyestradiol ("Cont-P"). "2-HE-1", "2-HE-3" and "2-HE-10" indicate 1, 3 and 10 ug/kg/hr 2-hydroxyestradiol, respectively, in males and "2-HE-F" indicates 10 ug/kg/hr 2-hydroxyestradiol in females. "2-ME-1", "2-ME-3" and "2-ME-10" indicate 1, 3 and 10 ug/kg/hr 2-methoxyestradiol, respectively, in males.
Figure 9:
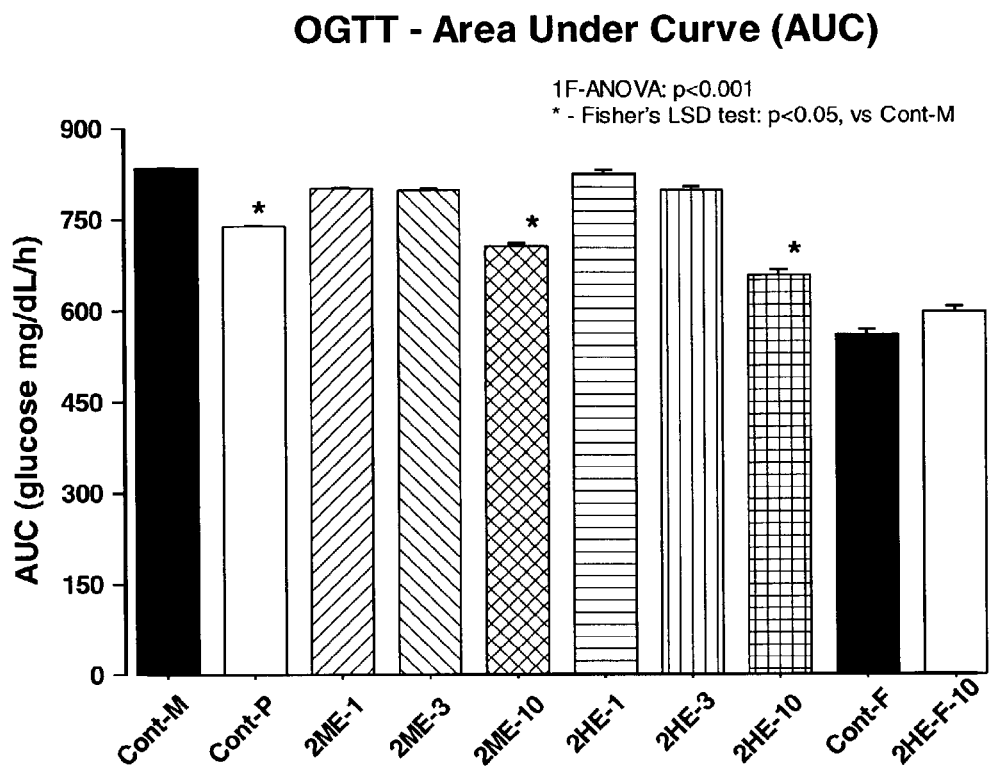
FIG. 9 shows effects of treatment with 1, 3 or 10 ug/kg/hr 2-hydroxyestradiol or 2-methoxyestradiol for 14 to 15 weeks on plasma glucose levels in an oral glucose tolerance test over 120 minutes expressed as area under the glucose concentration curve in male or female ZSF1 rats compared with untreated males ("Cont-M"), untreated females ("Cont-F") and untreated males pair fed to the 10 ug/kg/hr dose of 2-hydroxyestradiol ("Cont-P"). "2HE-1", "2HE-3" and "2HE-10" indicate 1, 3 and 10 ug/kg/hr 2-hydroxyestradiol, respectively, in males and "2HE-F-10" indicates 10 ug/kg/hr 2-hydroxyestradiol in females. "2ME-1", "2ME-3" and "2ME-10" indicate 1, 3 and 10 ug/kg/hr 2-methoxyestradiol, respectively, in males.

In addition, male animals treated for 14 to 15 weeks with 10 ug/kg/hr 2-hydroxyestradiol or 2-methoxyestradiol clearly demonstrated a lower plasma level of glucose (mg %) than control groups after administration of 2 g/4 ml/kg glucose (see FIGS. 8 and 9). Female animals demonstrated lower baseline levels of plasma glucose than male animals. Administration of glucose caused an initial increase in plasma glucose levels, which quickly dropped off to a level that was significantly lower than that found in male animals. With initial low levels of plasma glucose, administration of estradiol metabolites had little effect on plasma glucose levels as they were already at an acceptable level.

Figure 10:
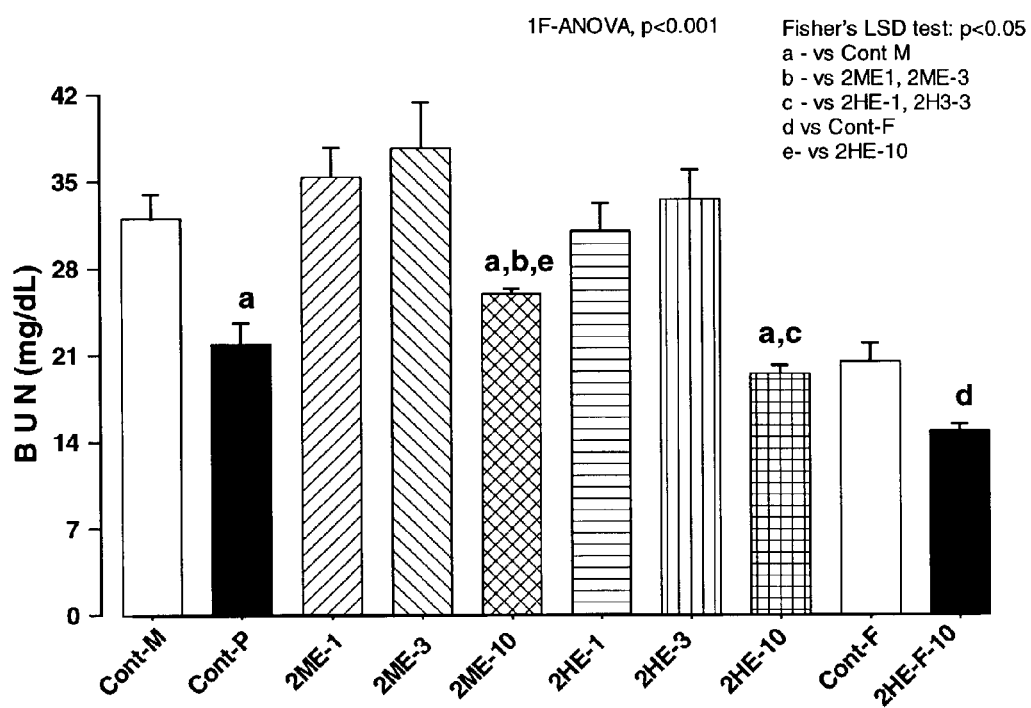
FIG. 10 shows effects of treatment with 1, 3 or 10 ug/kg/hr 2-hydroxyestradiol or 2-methoxyestradiol for 24 weeks on blood urea nitrogen ("BUN") levels in male or female ZSF1 rats compared with untreated males ("Cont-M"), untreated females ("Cont-F") and untreated males pair fed to the 10 ug/kg/hr dose of 2-hydroxyestradiol ("Cont-P"). "2HE-1", "2HE-3" and "2HE-10" indicate 1, 3 and 10 ug/kg/hr 2-hydroxyestradiol, respectively, in males and "2HE-F-10" indicates 10 ug/kg/hr 2-hydroxyestradiol in females. "2ME-1", "2ME-3" and "2ME-10" indicate 1, 3 and 10 ug/kg/hr 2-methoxyestradiol, respectively, in males.

Both male and female animals treated for 24 weeks with 10 ug/kg/hr 2-hydroxyestradiol or 2-methoxyestradiol demonstrated lower blood urea nitrogen than control groups (see FIG. 10).

Figure 11:
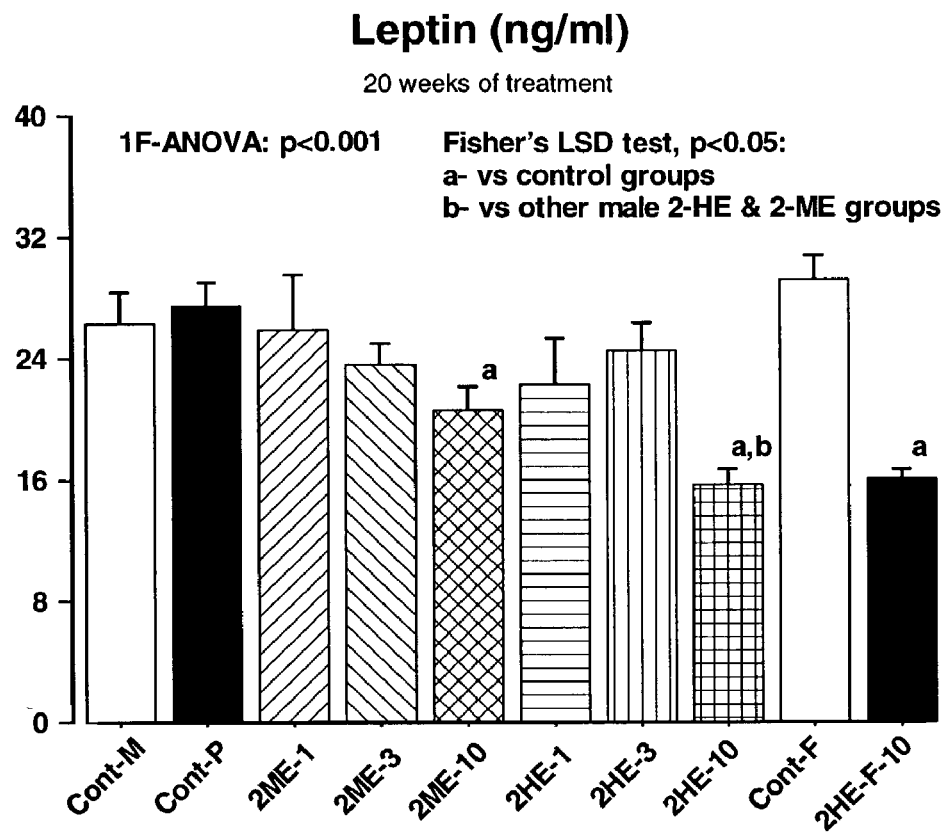
FIG. 11 shows effects of treatment with 1, 3 or 10 ug/kg/hr 2-hydroxyestradiol or 2-methoxyestradiol on plasma leptin levels at 20 weeks of treatment in male or female ZSF1 rats compared with untreated males ("Cont-M"), untreated females ("Cont-F") and untreated males pair fed to the 10 ug/kg/hr dose of 2-hydroxyestradiol ("Cont-P"). "2HE-1", "2HE-3" and "2HE-10" indicate 1, 3 and 10 ug/kg/hr 2-hydroxyestradiol, respectively, in males and "2HE-F-10" indicates 10 ug/kg/hr 2-hydroxyestradiol in females. "2ME-1", "2ME- 3" and "2ME-10" indicate 1, 3 and 10 ug/kg/hr 2-methoxyestradiol, respectively, in males.

Leptin levels in male animals were clearly reduced after treatment with 10 ug/kg/hr 2-hydroxyestradiol or 2-methoxyestradiol for 20 weeks when compared to control animals (see FIG. 11). Similarly, leptin levels in female animals treated with 10 ug/kg/hr 2-hydroxyestradiol were also reduced when compared to control animals (see FIG. 11).

Figure 12:
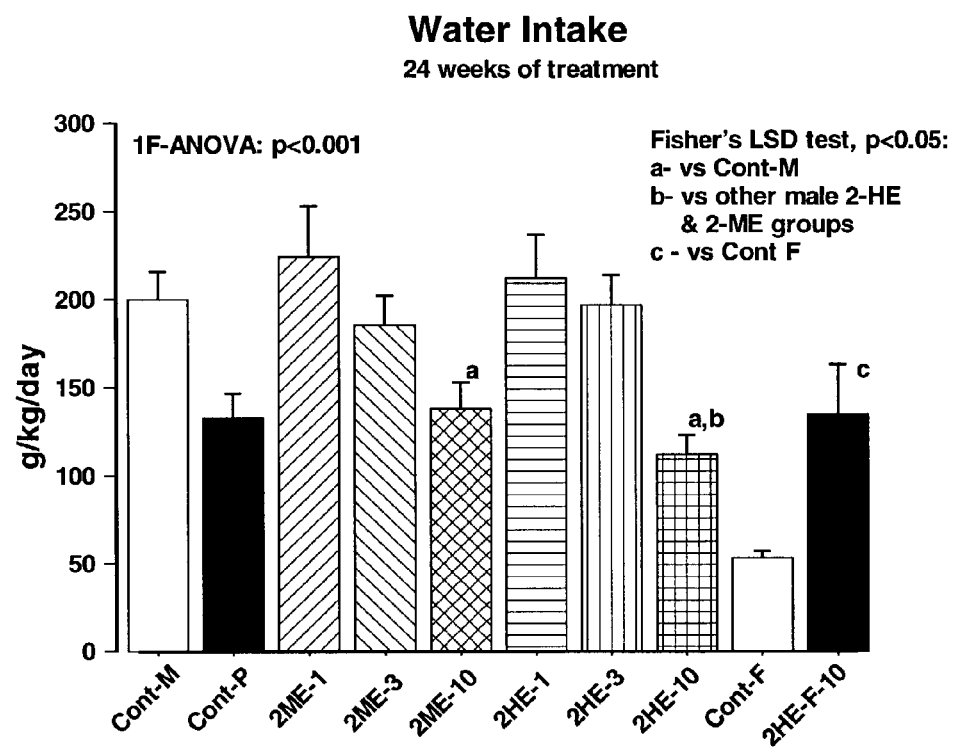
FIG. 12 shows 24-hour water intake following treatment for 24 weeks with 1, 3 or 10 ug/kg/hr 2-hydroxyestradiol or 2-methoxyestradiol in male or female ZSF1 rats compared with untreated males ("Cont-M"), untreated females ("Cont-F") and untreated males pair fed to the 10 ug/kg/hr dose of 2-hydroxyestradiol ("Cont-P"). "2HE-1", "2HE-3" and "2HE-10" indicate 1, 3 and 10 ug/kg/hr 2-hydroxyestradiol, respectively, in males and "2HE-F-10" indicates 10 ug/kg/hr 2-hydroxyestradiol in females. "2ME-1", "2ME-3" and "2ME-10" indicate 1, 3 and 10 ug/kg/hr 2-methoxyestradiol, respectively, in males.

Additionally, 24-hour water intake was lower in male animals treated with 10 ug/kg/hr 2-methoxyestradiol and 2-hydroxyestradiol when compared to control animals (see FIG. 12).

Figure 13:
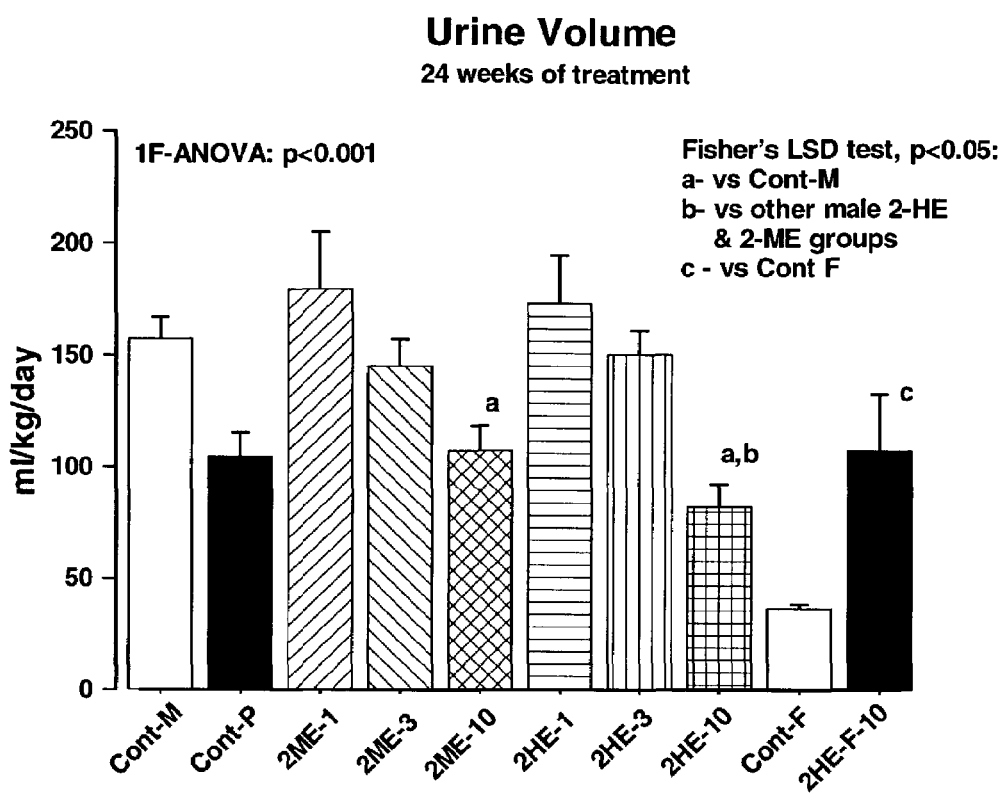
FIG. 13 shows 24-hour urine volume following treatment for 24 weeks with 1, 3 or 10 ug/kg/hr 2-hydroxyestradiol or 2-methoxyestradiol in male or female ZSF1 rats compared with untreated males ("Cont-M"), untreated females ("Cont-F") and untreated males pair fed to the 10 ug/kg/hr dose of 2-hydroxyestradiol ("Cont-P"). "2HE-1", "2HE-3" and "2HE-10" indicate 1, 3 and 10 ug/kg/hr 2-hydroxyestradiol, respectively, in males and "2HE-F-10" indicates 10 ug/kg/hr 2-hydroxyestradiol in females. "2ME-1", "2ME-3" and "2ME-10" indicate 1, 3 and 10 ug/kg/hr 2-methoxyestradiol, respectively, in males.
Figure 14:
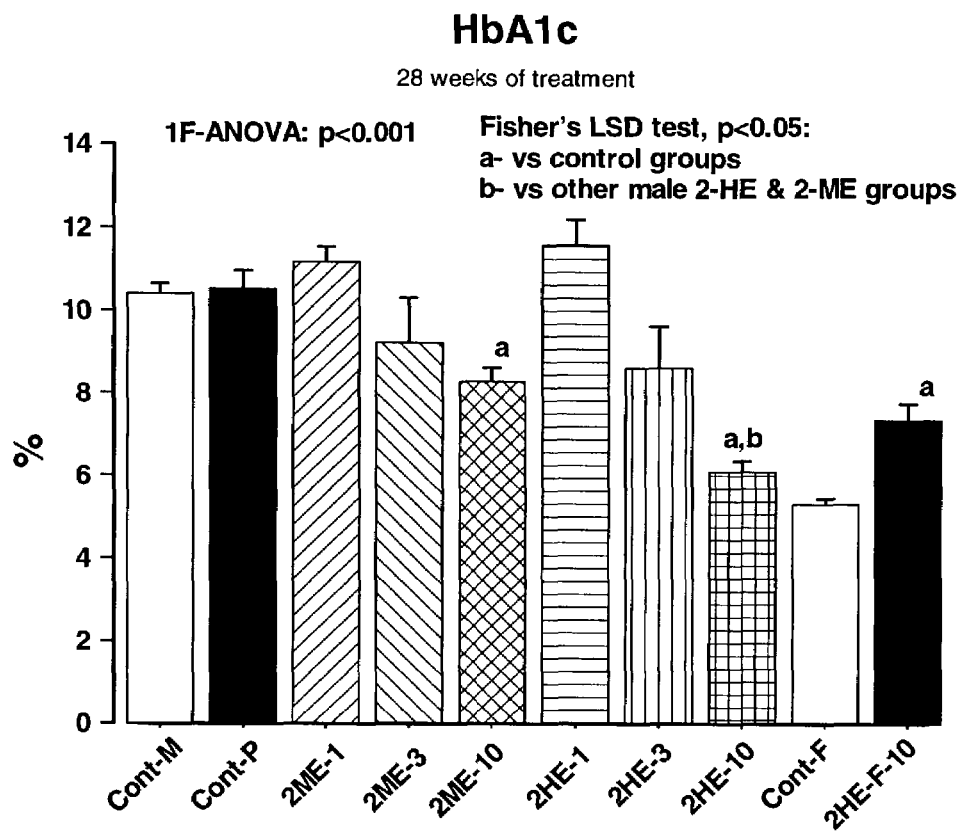
FIG. 14 shows glycated hemoglobin (HbA1c) following treatment for 28 weeks with 1, 3 or 10 ug/kg/hr 2-hydroxyestradiol or 2-methoxyestradiol in male or female ZSF1 rats compared with untreated males ("Cont-M"), untreated females ("Cont-F") and untreated males pair fed to the 10 ug/kg/hr dose of 2-hydroxyestradiol ("Cont-P"). "2HE-1", "2HE-3" and "2HE-10" indicate 1, 3 and 10 ug/kg/hr 2-hydroxyestradiol, respectively, in males and "2HE-F-10" indicates 10 ug/kg/hr 2-hydroxyestradiol in females. "2ME-1", "2ME-3" and "2ME-10" indicate 1, 3 and 10 ug/kg/hr 2-methoxyestradiol, respectively, in males.

24-hour urine output was also lower in male animals treated with 10 ug/kg/hr 2-methoxyestradiol and 2-hydroxyestradiol when compared to control animals (see FIG. 13).

Glycated hemoglobin (HbA1c) was also lower in male animals treated with 10 ug/kg/hr 2-methoxyestradiol and 2-hydroxyestradiol when compared to control animals.

While the disclosed methods and compositions have been described in terms of the specific embodiments of the invention, it will be apparent to those of ordinary skill in the art that variations may be applied without departing from the concept, spirit and scope of the claimed invention. More specifically, it will be apparent that certain agents that are both chemically and physiologically related may be substituted for the agents described herein while the same or similar results would be achieved. All such similar substitutes and modifications apparent to those skilled in the art are deemed to be within the invention as defined by the appended claims. Accordingly, it is understood that the drawings and the descriptions herein are proffered only to facilitate comprehension of the invention and should not be construed to limit the scope hereof.

What is claimed is:

1. A method for the treatment of diabetes mellitus in an individual, comprising: administering to said individual a therapeutically effective amount of a composition comprising an estradiol metabolite selected from the group consisting of 2-methoxyestradiol, 4-methoxyestradiol, 2-hydroxyestradiol and 4-hydroxyestradiol.

* * * * *